United States Patent [19]

Arena

[11] Patent Number: 4,487,980
[45] Date of Patent: Dec. 11, 1984

[54] METHOD FOR HYDROGENATING AQUEOUS SOLUTIONS OF CARBOHYDRATES

[75] Inventor: Blaise J. Arena, Des Plaines, Ill.

[73] Assignee: UOP Inc., Des Plaines, Ill.

[21] Appl. No.: 489,925

[22] Filed: Apr. 29, 1983

Related U.S. Application Data

[63] Continuation-in-part of Ser. No. 340,614, Jan. 19, 1982, Pat. No. 4,382,150.

[51] Int. Cl.$^3$ .............................................. C07C 31/26
[52] U.S. Cl. .................................... 568/863; 502/326
[58] Field of Search ........................................ 568/863

[56] References Cited

U.S. PATENT DOCUMENTS 3,055,840  9/1962  Koch .................................... 568/881

FOREIGN PATENT DOCUMENTS 354196  8/1931  United Kingdom ................ 568/863

Primary Examiner—J. E. Evans
Attorney, Agent, or Firm—James R. Hoatson, Jr.; Eugene I. Snyder; William H. Page, II

[57] ABSTRACT

Zerovalent Group VIII metals dispersed on titanium dioxide reduced and calcined at a temperature less than about 300° C. are hydrothermally stable hydrogenation catalysts which may be used advantageously in the reduction of aqueous solutions of carbohydrates. The use of ruthenium on titanium dioxide in the hydrogenation of glucose affords sorbitol in excellent yields with quite high selectivity.

11 Claims, No Drawings

METHOD FOR HYDROGENATING AQUEOUS SOLUTIONS OF CARBOHYDRATES

CROSS REFERENCE TO RELATED APPLICATION

This application is a continuation-in-part of my co-pending application, Ser. No. 340,614, filed Jan. 19, 1982, now U.S. Pat. No. 4,382,150, all of which is incorporated by reference.

BACKGROUND OF THE INVENTION

In hydrogenating organic materials using zerovalent metal catalysts, it is more common to use the metal dispersed on an inert support than to use, for example, colloidal dispersions of the metal itself. Included among advantages accruing to supported metals are their greater surface area, leading to increased reactivity, and their greater ease of separation, as by filtration. Colloidal metals are notoriously difficult to separate by filtration, and incomplete removal and recovery is costly and often deleterious to the product of hydrogenation.

When hydrogenations are conducted in aqueous media, the lack of hydrothermal stability of the commonly used supports places severe limitations on catalyst lifetime and recovery and also on the quality of the product due to dissolved support material. Where such hydrogenations are of hydroxylic organic compounds, the problem of hydrothermal instability of support materials is intensified. Where the organic compounds are polyhydroxylic, such as carbohydrates, the problem of hydrothermal instability is particularly exacerbated because of the relatively high concentration of hydroxyl groups from both water as solvent and the material to be hydrogenated.

The irony in hydrogenating aqueous solutions of carbohydrates is two-fold. First, the reduction products of many carbohydrates are important materials of commerce; sorbitol and mannitol are but two common reduction products. Second, there is no practical alternative to using water as the solvent in hydrogenating carbohydrates because carbohydrates generally are insoluble or, at best, sparingly soluble in most organic solvents. Because carbohydrates are solids, it is operationally mandatory to use a solvent in their hydrogenation.

Therefore, it is an object of this invention to hydrogenate carbohydrates in aqueous media using as a catalyst a zerovalent metal on a hydrothermally stable support. An embodiment comprises a method of hydrogenating an aqueous solution of a carbohydrate where the catalyst is certain Group VIII zerovalent metals dispersed on a support of titanium dioxide, $TiO_2$. In a more specific embodiment, the metal is ruthenium. In a still more specific embodiment, the carbohydrate is a hexose.

DESCRIPTION OF THE INVENTION

The invention which is the subject matter herein is a method for the hydrogenation of a carbohydrate in aqueous solution to its polyols comprising contacting at hydrogenation conditions a reaction medium consisting essentially of said solution with hydrogen and a catalyst consisting essentially of a zerovalent Group VIII metal selected from the group consisting of cobalt, ruthenium, palladium, platinum, and osmium dispersed on titanium oxide, and recovering the formed polyols. This invention results from the discovery that titanium dioxide possesses remarkable hydrothermal stability under conditions necessary for the hydrogenation of aqueous solutions of carbohydrates. Thus, whereas substantial amounts of silica and alumina, which are two commonly employed support materials, dissolve in the aqueous medium during hydrogenation of carbohydrates, virtually no leaching of titanium dioxide occurs under comparable hydrogenation conditions.

Therefore, one advantage of this invention is that the product contains a substantially lower level of dissolved metal from the inert support described herein than that resulting from inert supports commonly employed previously in the hydrogenation of aqueous solutions of carbohydrates.

Another advantage of this invention is that the zerovalent metals commonly employed as a hydrogenation catalyst retain their activity on the titanium dioxide support of this invention.

Still another advantage is that the results of hydrogenation may be altered by changing the temperature of reduction of the metal on titanium dioxide. Thus, one may exert control over the product distribution by the novel technique of changing the reduction temperature.

Yet another advantage of that branch of the invention relating to ruthenium is that because ruthenium is both resistant to leaching and particularly catalytically active it is especially advantageous in the practice of this invention.

The invention herein is concerned with a method of hydrogenating a carbohydrate to its polyols. Carbohydrates are polyhydroxyaldehydes, polyhydroxyketones, or compounds that can be hydrolyzed to them. A carbohydrate that cannot be hydrolyzed to simpler compounds is called a monosaccharide. One that can be hydrolyzed to two monosaccharide molecules is called a disaccharide, and one that can be hydrolyzed to many monosaccharide molecules is called a polysaccharide. A monosaccharide may be classified according to the number of carbon atoms it contains; a hexose is a 6-carbon monosaccharide, a pentose is a 5-carbon monosaccharide, and a tetrose is a 4-carbon monosaccharide. Monosaccharides are preferred among the carbohydrates which may be used in this invention, and among these the hexoses, pentoses and tetroses are the most important members, with the hexoses being particularly preferred.

The polyol reduction products of this invention have the formula $HOCH_2(CHOH)_nCH_2OH$, where n is 2, 3, or 4 depending upon the kind of monosaccharide used or the kind of units in the di- or polysaccharide. Where n is 4, the polyol is a hexitol; where n is 3, the polyol is a pentitol; and where n is 2, the polyol is a tetritol. It is to be understood that where the carbohydrate is a disaccharide or polysaccharide, substantial hydrolysis accompanies hydrogenation to ultimately afford the polyols of this invention.

The examples of carbohydrates below are cited merely for illustration, and are not intended as exhaustive of the suitable reactants which may be used in this invention. Accordingly, monosaccharides that can be employed include glucose, mannose, galactose, talose, fructose, allose, altrose, idose, gulose, xylose, lyxose, ribose, arabinose, threose and erythrose. Glucose and mannose are particularly preferred monosaccharides which afford sorbitol and mannitol, respectively, as their polyol reduction product. Fructose is another preferred monosaccharide which affords a mixture of sorbitol and mannitol as the product. Examples of disaccharides include maltose, cellobiose, sucrose and lactose. Among the more abundant polysaccharides which may be employed in this invention are starch, cellulose and their degradation products.

The catalysts of this invention consist essentially of one or more of certain zerovalent Group VIII metals dispersed on titanium dioxide. Among the metals which may be used are included cobalt, ruthenium, osmium, palladium and platinum, with ruthenium being preferred because of its relatively greater resistance to leaching and higher activity.

The Group VIII metal is generally dispersed on titanium dioxide as the inert support by impregnating the latter with a suitable salt of the metal, calcining the salt where necessary, followed by reduction to the zerovalent metal in a hydrogen atmosphere. Calcining is performed where volatiles are to be removed from the support, or where the metal salt needs to be converted, e.g., to its oxide, to be readily reducible. In suitable cases calcination and reduction may be combined in the same step. The temperature of reduction has a substantial influence on the catalyst in the process of this invention. Thus, it has been found that where reduction is performed at a temperature less than about 300° C., the resulting catalyst effects maximum conversion of the carbohydrate with maximum formation of its polyol hydrogenation product(s). The lower limit of reduction temperature is not critical and is dictated by the desire to have a reasonable rate for reduction of the metal. It is preferred that the temperature be from about 100° to about 300° C. with a temperature from about 150° to about 250° C. being even more desirable. Where the reduction temperature used in the preparation of the catalyst is greater than about 300° C., the resulting catalyst may cause isomerization of the carbohydrate and exhibits somewhat lower hydrogenation activity. The amount of metal on titanium dioxide is not particularly critical. Concentrations up to about 25 percent by weight metal may be employed, although concentrations from about 0.1 to about 10 percent are more common.

The aqueous solution of the carbohydrate is contacted with hydrogen and the catalyst of this invention at hydrogenation conditions. Hydrogenation conditions include a pressure of at least about 200 psig, with pressures in excess of about 2500 psig generally not advantageous. In the usual case, a hydrogen pressure from about 500 to about 2000 psig is used. The hydrogenation temperature will be greater than about 80° C., with the upper temperature limit dictated by the onset of the decomposition of either the product or reactant. For example, in the case of glucose as the reactant and sorbitol as the product, the upper temperature limit is about 160° C. In practical terms, a hydrogenation temperature from about 100° to about 150° C. is preferred with one from about 105° to about 130° C. being especially advantageous.

The amount of catalyst used will depend, inter alia, on the amount of metal on the support, hydrogenation pressure, and temperature. For example, in the case where the metal is ruthenium sufficient catalyst is employed to give from about 0.1 to about 1 wt. % ruthenium based on the carbohydrate as monosaccharide.

The method of this invention may be practiced in either a batch or a fixed mode. In the batch mode, an aqueous solution of the carbohydrate containing from about 15 to about 50 percent carbohydrates is loaded into a reactor containing, for example, the ruthenium on titanium dioxide catalyst of this invention in an amount sufficient to give from about 0.1 to about 1 wt. % ruthenium based on the carbohydrate. The mixture is then heated to the desired temperature, which is from about 80° to about 160° C., and usually from about 100° to about 150° C. After the desired reaction temperature is attained, hydrogen is admitted to a pressure from about 500 to about 2000 psig. The entire reaction mixture is then agitated to provide adequate contact among the hydrogen, catalyst, and carbohydrate. The hydrogenation is continued until there is no further hydrogen uptake, which generally is a time from about 0.5 to about 5 hours.

The invention described is advantageously practiced in a continuous fashion using the catalyst in a fixed bed, fluidized bed, expanded bed, and so forth. In a typical operation, feedstock containing from about 15 to about 50% of the carbohydrate(s) to be reduced is passed through the bed of, e.g., ruthenium on titanium dioxide in a hydrogen atmosphere. Hydrogen pressure is from about 500 to about 2000 psig, and bed temperature is generally from about 100° to about 150° C. The effluent is an aqueous solution of the formed polyol(s), which may be recovered, for example, by removal of water by evaporation.

The examples which follow merely illustrate this invention and are not intended to limit it in any way.

EXAMPLE I

The following experiment was done to demonstrate the hydrothermal stability of various materials often used as an inert support for catalytically active zerovalent metals. A mixture of 50 ml of a 50 percent aqueous solution of sorbitol and 2.5 g of support material was held in a rotating glass-lined autoclave for 24 hours in the presence of hydrogen at 135 atmospheres and at 130° C. At the end of this period, solid was removed by filtration and the filtrate was analyzed for metals. The following table summarizes the results.

| LEACHING OF INERT SUPPORTS | |
|---|---|
| Support Material | Dissolved Support Material |
| $TiO_2$—bentonite (90% $TiO_2$) | less than 1 ppm Ti; 93 ppm Si |
| gamma-alumina[a] | 60 ppm Al |
| gamma-alumina[b] | 129 ppm Al |
| kieselguhr[c] | 83 ppm Si |

[a] 0.5. ABD, SA 200 $m^2/g$
[b] 0.3 ABD, SA 160 $m^2/g$
[c] Solution of glucose was used instead of sorbitol.

The results clearly show the superior hydrothermal stability of titanium dioxide relative to other commonly employed supports.

EXAMPLE II

The following description is representative of the preparation of the supported catalysts of this invention. A solution of 0.335 g $RuCl_3.3H_2O$ in 150 ml deionized water was mixed with 14.6 g titanium dioxide for 0.5 hour. Water then was removed by evaporation at 105° C. About half of the resulting material was reduced in flowing hydrogen at 220° C. for 3 hours, and the other half was reduced in flowing hydrogen at 400° C. for 3 hours. Each of the resulting catalyst preparations was about 1% ruthenium by weight.

EXAMPLE III

A mixture of about 50 ml of a 50% aqueous glucose solution and 2.0 g catalyst as prepared in Example II was contacted with hydrogen at 700 psig and 100° C. for 5 hours in a rotating glass-lined reactor. The catalyst reduced at 220° C. afforded 71.1% conversion; that reduced at 400° C. afforded 67.0% conversion.

EXAMPLE IV

Continuous hydrogenations may be performed in a ⅜" I.D. vertical tube reactor with a spiral preheater using a bed of 50 cc 1% ruthenium catalyst as prepared in Example 2 at a reduction temperature of 220° C. Using a 50% aqueous solution of glucose as the feedstock in an upflow mode, hydrogenation may be performed at 110° C. under 2300 psig hydrogen and 1.0 liquid hourly space velocity with a hydrogen-to-glucose flow ratio of 10:1. Under these conditions glucose conversion of 99% may be attained with 96% selectivity to sorbitol. Levels of ruthenium and titanium in the product may be less than 1 ppm.

What is claimed is:

1. A method for the hydrogenation of a carbohydrate in aqueous solution to its polyols comprising contacting at hydrogenation conditions a reaction medium consisting essentially of said solution with hydrogen and a catalyst consisting essentially of from about 0.1% to about 25% of a zerovalent metal selected from the group consisting of ruthenium, palladium, and platinum dispersed on titanium dioxide, and recovering the formed polyols.

2. The method of claim 1 where the carbohydrate is a monosaccharide.

3. A method of claim 2 where the monosaccharide is selected from the group consisting of hexoses, pentoses, and tetroses.

4. The method of claim 3 where the monosaccharide is a hexose and the polyol is a hexitol.

5. The method of claim 4 where the hexose is glucose or mannose and the hexitol is sorbitol or mannitol, respectively.

6. The method of claim 4 where the hexose is fructose and the polyol is a mixture of sorbitol and mannitol.

7. The method of claim 1 where the metal-titanium dioxide combination has been reduced at a temperature less than about 300° C.

8. The method of claim 1 where the metal is ruthenium.

9. The method of claim 1 where the hydrogenation conditions include a hydrogen pressure from about 200 to about 2500 psig and a temperature from about 80° to about 160° C.

10. The method of claim 9 where the pressure is from about 500 to about 2000 psig.

11. The method of claim 9 where the temperature is from about 100° to about 150° C.

* * * * *